(12) United States Patent
Gyles et al.

(10) Patent No.: US 8,959,200 B2
(45) Date of Patent: Feb. 17, 2015

(54) EVENT-BASED COMMUNICATION IN A CLINICAL DIAGNOSTIC ANALYZER

(75) Inventors: Trevor Gyles, Fairport, NY (US); Keith Arnold Baker, Spencerport, NY (US); Richard Peter Hemmenway, Hilton, NY (US); Christopher Thomas Doody, Shortsville, NY (US)

(73) Assignee: Ortho-Clinical Diagnostics, Inc., Raritan, NJ (US)

( * ) Notice: Subject to any disclaimer, the term of this patent is extended or adjusted under 35 U.S.C. 154(b) by 613 days.

(21) Appl. No.: 12/493,652

(22) Filed: Jun. 29, 2009

(65) Prior Publication Data

US 2010/0005344 A1  Jan. 7, 2010

Related U.S. Application Data (60) Provisional application No. 61/077,241, filed on Jul. 1, 2008.

(51) Int. Cl.
*G06F 15/173* (2006.01)
*G06F 19/00* (2011.01)

(52) U.S. Cl.
CPC ........ *G06F 19/3418* (2013.01); *G06F 19/3412* (2013.01)
USPC .......................................... 709/224; 709/217

(58) Field of Classification Search
CPC .............................. G06F 11/28; G06F 15/173
USPC ...................... 709/217, 224; 607/59
See application file for complete search history.

(56) References Cited

U.S. PATENT DOCUMENTS

| | | | |
|---|---|---|---|
| 5,838,906 A * | 11/1998 | Doyle et al. ................. | 715/205 |
| 6,377,162 B1 | 4/2002 | Delestienne et al. | |
| 6,418,448 B1 | 7/2002 | Sarkar | |
| 6,570,867 B1 | 5/2003 | Robinson et al. | |
| 6,662,199 B1 | 12/2003 | Flight et al. | |
| 6,757,714 B1 | 6/2004 | Hansen | |
| 6,768,968 B2 | 7/2004 | Ignatowski et al. | |
| 6,892,317 B1 | 5/2005 | Sampath et al. | |
| 6,976,020 B2 | 12/2005 | Anthony et al. | |
| 6,980,558 B2 | 12/2005 | Aramoto | |
| 7,031,782 B2 | 4/2006 | Kappelhoff et al. | |

(Continued)

FOREIGN PATENT DOCUMENTS

| | | |
|---|---|---|
| CN | 1540566 A | 10/2004 |
| CN | 101088092 A | 12/2007 |

(Continued)

OTHER PUBLICATIONS

European Search Report, EP 09 25 1701, Dated Oct. 19, 2009.

*Primary Examiner* — Emmanuel L Moise
*Assistant Examiner* — Marie Georges Henry
(74) *Attorney, Agent, or Firm* — Rattan Nath (57) ABSTRACT

A networked clinical diagnostic analyzer is disclosed with support for monitoring by a remote back office. The disclosed analyzer includes a module to detect in real-time events of interest while allowing the back office to modify the definitions of the events. The module may be networked using virtual private networking into the back office network, which is usually different from the network at the site of the clinical diagnostic analyzer's deployment. The real-time alerts allow both a quick response to actual or expected error conditions and the downloading of logged data that is likely of most interest and relevance.

19 Claims, 5 Drawing Sheets

(56) References Cited

U.S. PATENT DOCUMENTS

| | | |
|---|---|---|
| 7,046,134 B2 | 5/2006 | Hansen |
| 7,082,460 B2 | 7/2006 | Hansen et al. |
| 7,117,239 B1 | 10/2006 | Hansen |
| 7,143,155 B1 | 11/2006 | Reed et al. |
| 7,149,792 B1 | 12/2006 | Hansen et al. |
| 7,178,149 B2 | 2/2007 | Hansen |
| 7,237,223 B2 | 6/2007 | Leu et al. |
| 7,251,588 B2 | 7/2007 | Graupner et al. |
| 7,254,601 B2 | 8/2007 | Baller et al. |
| 7,284,194 B2 | 10/2007 | Gupta |
| 7,640,308 B2 * | 12/2009 | Antonoff et al. ............. 709/206 |
| 2002/0116550 A1 | 8/2002 | Hansen |
| 2003/0149934 A1 | 8/2003 | Worden |
| 2004/0102683 A1* | 5/2004 | Khanuja et al. ............. 600/300 |
| 2004/0177124 A1 | 9/2004 | Hansen |
| 2005/0283385 A1* | 12/2005 | Hunkeler et al. ............. 705/2 |
| 2006/0112213 A1 | 5/2006 | Suzuoki et al. |
| 2007/0005736 A1 | 1/2007 | Hansen et al. |
| 2007/0011295 A1 | 1/2007 | Hansen |
| 2007/0078976 A1* | 4/2007 | Taylor et al. ............. 709/224 |
| 2007/0112827 A1 | 5/2007 | Dettinger et al. |
| 2007/0150903 A1* | 6/2007 | Hansen ............. 719/315 |
| 2007/0198661 A1 | 8/2007 | Hansen |
| 2007/0276452 A1* | 11/2007 | Sanghera et al. ............. 607/59 |
| 2007/0288629 A2 | 12/2007 | Taylor et al. |

FOREIGN PATENT DOCUMENTS

| | | |
|---|---|---|
| CN | 101183932 A | 5/2008 |
| JP | 2001-325352 A | 11/2001 |
| JP | 2007-189477 A | 7/2007 |
| JP | 2007-274416 A | 10/2007 |
| WO | 03/088830 A1 | 10/2003 |
| WO | WO 2004070557 A2 | 8/2004 |
| WO | 2006/067725 A2 | 6/2006 |
| WO | 2006/119370 A3 | 11/2006 |
| WO | 2007/027570 A1 | 3/2007 |

* cited by examiner

EVENT-BASED COMMUNICATION IN A CLINICAL DIAGNOSTIC ANALYZER

BACKGROUND

Estimating the expected performance and monitoring the actual performance of clinical laboratory testing and diagnostic systems requires detailed and current information. Clinical laboratory testing and diagnostic systems include many components and subsystems in a complex coordinated combination for carrying out accurate assays while maintaining a high throughput. As example is provided by the VITROS 5600™ and ECi line of clinical Diagnostic Analyzers manufactured by Ortho Clinical Diagnostics ("OCD") of Raritan, N.J.

Laboratories differ significantly in their use of laboratory testing and diagnostic systems. Physicians need fast turn-around times for results to allow them to effectively monitor patients under care. For instance, patients with kidney problems or trauma need to be evaluated and monitored to properly manage their electrolyte levels. Further, local needs result in different mixes of tests in different clinical laboratories, which may require customized approaches for evaluating analyzer performance.

Testing to ensure a high level of reliability preferably includes monitoring aimed at both quick servicing times and improving analyzer performance. To this end, an embedded controller is often relied upon to periodically provide data and to log the huge number of events reflecting analyzer operation. This data is uploaded at a fixed time, for instance, at mid-night, and the like. Such data is not only stale but voluminous making the task of analyzing events of interest tedious.

Embedded controllers, also referred to as "embedded devices", in a clinical diagnostic analyzer are often connected to an internal network, such as a local area network (LAN), wireless IEEE (Institute of Electrical & Electronics Engineers) 802.11, wireless broadband, or HomePlug powerline, with an interface to the Internet. The embedded device is typically behind a firewall, which prevents it from being addressed or discovered directly by an external monitoring system.

This limitation on the use of embedded devices is expected due to the need to keep networks secure and protect patient data. As a result, it is difficult, if not impractical, to freely monitor a clinical diagnostic analyzer installed at a remote site. Some monitoring approaches have been proposed, some of which balance the need to monitor against the requirement to maintain a secure environment for sensitive data.

U.S. Pat. No. 6,768,968 (the "'968 patent") discloses a strategy for estimating the performance of a computer system. While a clinical diagnostic analyzer includes processing power, it is not quite like a computer system in view of its highly specialized properties. The '968 patent discloses some monitoring strategies without adequate consideration of the privacy needs. The computer in a diagnostic analyzer is integrated with electrical and mechanical parts for accurately testing biological materials—the primary purpose of the device. This integrated design is susceptible to failures that are not analogous to those experienced by computer systems.

U.S. Pat. No. 7,254,601 (the "'601 patent") discloses a method for managing remotely deployed intelligent equipment by establishing a direct computer-based connection to remote equipment through Internet standard protocols and a Gateway, which masquerades for a set of assets, translates addresses, and provides necessary protocol conversions needed to "speak the native language of the enterprise." The '601 patent discusses the need to get past firewalls noting that most firewalls permit HTTP traffic, the protocol used by browsers to retrieve web pages, which access may be used to provide web services based on text messages formatted with eXtensible Markup Language (XML), to package requests as messages. Some such standards include WSDL (Web Service Description Language), SOAP (Simple Object Access Protocol), and XML. The disclosure does not, however, teach providing real-time alerts.

U.S. Pat. No. 6,377,162 (the "'162 patent") discloses a field service unit for providing interactive field service of medical diagnostic systems generating images. The '162 patent does not disclose or address the failures encountered by clinical diagnostic analyzers because it is focused on systems generating images, such as resulting from X-ray scans.

US Patent Publication No. 2007/0288629 (the "'629 publication") discloses sending fault information outside of a firewall by periodically sending a polling call to an enterprise system outside the firewall at a first polling rate during normal operating conditions, and sending polling calls to the device outside the firewall at a second polling rate in response to detecting a fault condition. The second polling rate is higher than the first polling rate. The method includes sending a problem report with the polling calls when the fault condition is detected. Sending the request from within the firewall allows opening of a two-way connection through the firewall between the device inside the firewall and the external system. However, in the absence of a polling message from inside the firewall, the embedded device remains undiscoverable by the systems outside the firewall.

U.S. Pat. No. 6,757,714 (the "'714 patent") and patents and patent applications related thereto disclose obtaining and communicating an error condition of an apparatus—via email to a remote server. A predefined template is used to generate the e-mail message by obtaining and inserting one or more variables into the template. The error condition may be included as part of a body of the e-mail message or as part of an attachment to the e-mail message. The error condition is reported using a self-describing computer language, such as eXtensible Markup Language (XML). In general, the error condition is determined with the aid of an embedded controller. The remote server passes the error condition to a customer relationship management system.

In the '714 patent's disclosure, e-mail allows the remote server to obtain information about the apparatus even if the remote server cannot directly address the embedded controller. Email can provide information, for instance if the remote server is not on the same internal network as the embedded controller. Moreover, because the error condition is reported using XML, the remote server may automatically schedule maintenance. As may be expected, the emails in such a system contain state information for extraction by the monitoring system. The '714 patent limits error notifications to detecting predefined events with no ability to customize alerts to detect other than predefined events.

Another option for monitoring clinical diagnostic analyzers is to transmit a program to the target analyzer to reprogram it. Programming a remote device using XML coding is described in U.S. Pat. No. 7,178,149. Such programming, however, significantly increases the complexity of the task of monitoring the analyzers because each command of the programming language is made to correspond to a tag in XML with the overhead of XML added to make the transmitted program code quite voluminous. At the target device, the XML encoded program may need to be not only decoded, but potentially also compiled and run. Thus, the overhead at the target remote device is also significantly higher. XML itself is merely a text transmission method in such an implementation, no different from sending an email containing program code. These considerations make this approach unsuitable for customized remote monitoring of a clinical diagnostic analyzer.

Alternatively complex circuits and functionalities can be implemented to monitor a networked device in a distributed system such as those described in U.S. Pat. No. 6,892,317. This would not work, however, with clinical diagnostic analyzers in different networks protected by firewall. Thus, there is a need for better monitoring of clinical diagnostic analyzers.

SUMMARY

Embodiments disclosed herein provide a system and method for customizable monitoring of events at a remote clinical diagnostic analyzer. The described embodiments overcome the challenges described above.

Briefly, in a preferred embodiment, (a) an efficient and flexible coding strategy is employed to specify and customize the monitored events, (b) the clinical diagnostic analyzer is integrated into two networks without compromising privacy to provide the required access to and by the embedded device for reporting alerts, and (c) real-time alerts are generated in response to detection of a customized event to allow both a quick response and remote transmission of the relevant logged data The preferred embodiment generates alerts in response to detecting one or more of a group of customized events. The customized event is described by logically combining basic events predefined for the clinical diagnostic analyzer. Consequently, it is possible to customize events, for instance, to improve error prediction, error detection and service with remote monitoring of the analyzer.

When an alertable event is detected, it is logged and a message is sent back to the external monitor. A server at the external monitor then handles the message as required.

In another aspect, a preferred embodiment includes a module for communicating real-time alerts generated at the clinical diagnostic analyzer to the external monitor. The module comprises a customized event detection sub-module for detecting customized events. A connection sub-module provides a link to the external monitor, wherein the external monitor is linked to the clinical diagnostic analyzer via a secure network connection. Customized events may be updated via a sub-module for dynamically updating customized events. A data-logging facility facilitates logging information being sent to or retrieved by the external monitor.

In a preferred embodiment, the embedded module has two network addresses. The clinical diagnostic analyzer, typically, is placed in a first network with firewalls and other safeguards to preserve patient privacy. The embedded module is preferably connected to the external monitor, in a second network, through a virtual private network link that tunnels through the Internet. The external monitor is external to the first network and the Internet is accessed via the first network to complete the link between the embedded module and external monitor in the second network. Thus, the embedded module can be treated as being a part of the second network for performing limited tasks that do not involve or require access to patient identifying information.

In the second network, the embedded module and the external monitor are on the same subnet. This subnet is preferably further isolated from other parts of the second network to protect and isolate communications relating to the clinical diagnostic analyzer.

Preferably, the module causes posting to a webpage to communicate alerts to the external monitor. The external monitor may use protocols such as the File Transfer Protocol, or a GET command in the Hyper Text Transfer Protocol to access logged data at the clinical diagnostic analyzer. Generally, the embedded module comprises a circuit for detecting a customized event at the clinical diagnostic analyzer; a circuit for communicating an alert to the external monitor; a circuit for dynamically updating the customized events; and a circuit for logging information to be sent or retrieved by the external monitor.

The circuit for implementing changes in the customized events preferably receives changes as instructions coded in XML such that at least one logical operation specified in the changes is encoded in the order and context of XML tags and not by a specific tag.

The circuit for detecting customized events interprets instructions to identify customized events when they occur. In a preferred embodiment, a logical operation specified by the instructions for combining basic events is encoded in the order and context of tags in XML instead of a specific tag.

Advantageously, the embedded module can be addressed directly by the external monitor using the VPN link. As a result, the circuit for logging information is implemented to allow limited access to log files by the external monitor periodically or in response to a report of a customized event detected by the module. The limited access protects patient privacy while allowing adequate access to allow effective monitoring of the analyzer. Even this limited access can be denied readily as is apparent to one having ordinary skill in the art.

A preferred method is performed at a suitably designed module for communicating real-time alerts generated at a clinical diagnostic analyzer to an external monitor. The method comprises facilitating the steps of detecting customized events at the clinical diagnostic analyzer; communicating in real time, in response to detection of a customized event, with the external monitor, wherein the external monitor is linked to the clinical diagnostic analyzer via a secure network connection; changing the customized events in response to instruction received from the external monitor; and logging information to be sent to or retrieved by the external monitor.

The customized events may be dynamically specified. Preferably, the instructions describing the customized events received from the external monitor are coded in XML such that at least one logical operation specified by the instructions is encoded in the order and context of tags rather than by a specific tag. The newly received instruction supersede the prior instructions, thereby dynamically customizing events. Further, in response to detecting a customized event, information is logged by writing to a datalog file, which aids in trouble-shooting and evaluating the performance of the analyzer.

These and other features in some preferred embodiments are described below in detail with the aid of illustrative figures, which are briefly described next.

DETAILED DESCRIPTION OF THE PREFERRED EMBODIMENTS

A 'basic event' in a clinical diagnostic analyzer, typically, is the detection of one or more parameters or a change therein. The parameters are values or descriptors of a state of a clinical diagnostic analyzer. An event occurs upon fulfillment of one or more specified conditions. A large number of such basic events are typically predefined for clinical diagnostic analyzers. Preferably, basic events of interest are described using eXtensible Markup Language ("XML") tags. Typically, such basic events are used to monitor the functioning of the analyzer while executing various commands. In general, XML tags or other descriptors may be defined for many or all basic events in a clinical diagnostic analyzer.

There are many advantages in using XML. XML is useful for defining events, including those that are combinations or variations of basic events. XML encoded instructions and descriptions can be implemented and debugged rapidly in real time using an interpreter. Further, XML based definitions are readily communicated by treating them as text. However, XML tags, although readable by humans, often describe very different functions and data using similar or even the same tag names. XML encoded instructions and descriptions can be implemented and debugged rapidly in real time using an interpreter. Further, XML based definitions are readily communicated by treating them as text. Nevertheless, in a context XML provides a description of the functions performed by executing XML compliant instructions. Therefore, given a proper context, XML provides a convenient method for communicating data, instructions and combinations thereof.

In effect, a specific instance of XML designed to facilitate a particular set of tasks at a target creates a "new machine" capable of performing particular functions. Thus, a circuit performing a function(s) specified by an one or more XML tags in response to interpreting XML encoded instructions is potentially a novel structure performing the indicated function(s).

In a preferred embodiment, basic events may be logically combined to define a customized event. For instance, a specified number of occurrences of an event over time may form a customized event of interest. An alert may be generated in the preferred embodiment in response to detecting such a customized event. In a preferred embodiment, events are customized by instructions coded in a markup language, such as XML for combining one or more basic events. Advantageously, at least one logical operation for combining is encoded in the order and context of XML tags and not by a specific tag. This reduces the number of tags needed to effectively specify events, and hence the complexity in customizing events.

Advantageously, at least one logical operation for combining events is encoded in the order, and possibly the context, of XML tags instead of a specific tag. This feature both adds to the clarity of the instructions and reduces the number of tags needed to customize events.

Events Based Alerts evaluate a clinical diagnostic analyzer and associated parameters against a set of rules established to identify specific scenarios occurring on the system. The scenarios, for instance, may be aimed at preventing failures before they occur (predictive maintenance) but also may be used to inform a service provider, which may be the manufacturer, about post failure scenarios. This is accomplished by providing the ability to customize events using basic events coded in XML or another representational system.

When the conditions for a scenario have been met, an event is logged on the system, and a message is sent back to through an external monitor server. The external monitor server then routes the message as needed.

Event Based Alerts are compatible with the design of OCD's clinical diagnostic analyzer VITROS 5600™ and VITROS 3600™, which provide a preferred platform for implementing such alerts, although Event Based Alerts are useful with other clinical diagnostic analyzers as well. Each of VITROS 5600™ and VITROS 3600™ use functions provided by a Master Scheduler, which can support the three chemistry platforms: (i) MicroSlides™ using dry chemistry, (ii) MicroTips™ for wet chemistry, and (iii) MicroWellS™ using wet chemistry. OCD's Master Scheduler can also control a robotic arm and pipettors shared between the various chemistry platforms to provide random access to input patient samples. As is apparent, alternative schedulers may be suitably modified to provide event based alerts.

OCD's Master Scheduler performs scheduling functions, for instance, to allocate resources to samples input in any order, without regard to the type or quantity of tests required, and to maintain or improve the throughput of the analyzer. OCD's Master Scheduler determines the test requirements of the two sets as a whole and determines a schedule to minimize the Time to Complete for the tests as a whole thereby maintaining high throughput.

OCD's Master Scheduler also supports implementation of tests based on multiple chemistries by allowing sharing of robotic arms and pipettors between the various platforms to manage sample throughput by providing random access to input samples. An innovative sample layout separates platforms for conducting various chemistries from the input samples to permit two-dimensional random sampling from the input samples. The two-dimensional random access to the input samples substantially eliminates the typical requirement to process samples in the order they are input.

The benefits of OCD's Master Scheduler include the synergistic effects of two-dimensional random access to the input samples while providing access to resources including, for example, multiple platforms, supply of consumables including thin film slides, reaction vessels and cuvettes, along with a plurality of sensiometric devices such as electrometers, reflectometers, luminescence, light transmissivity, photon detection, an incubator for heating the samples, a supply of reagents, and a plurality of reagent delivery subsystems, all of which can be accessed and used readily.

For controlling out each of these processes and tests, the scheduler issues a command to a subsystem. When the command is carried out, various measurements are made and a response message is sent back to the scheduler to confirm the command was carried out successfully based on the detected events to complete the loop. Nevertheless, errors in operation of clinical analyzers continue to be an expensive and undesirable reality. Accordingly, the message traffic between various parts of the analyzer may be monitored to implement various strategies to predict, preferably prevent or correct errors to reduce downtime for the clinical diagnostic analyzer.

This task is complicated by the fact that clinical analyzers handle patient samples requiring security to ensure privacy and confidentiality. They are also typically sited far away from either the manufacturer or repair service providers.

The disclosed embodiments facilitate monitoring of such remote clinical diagnostic analyzers without risking patient privacy or the security of the analyzer while allowing dynamic monitoring and prospective and retrospective trouble shooting at a back office or a designated site for providing service.

A module is logically self contained (although it may use shared resources) to perform its function. Resources typically are processor time slices, database data, data in memory shared with other modules, sub modules, shared library functions and the like as is well known to one having ordinary skill in the art. A developer, having ordinary skill in the art, knows how to create a module. Mapping functional partitioning into executable code is familiar to one having ordinary skill in the art.

Figure 1:
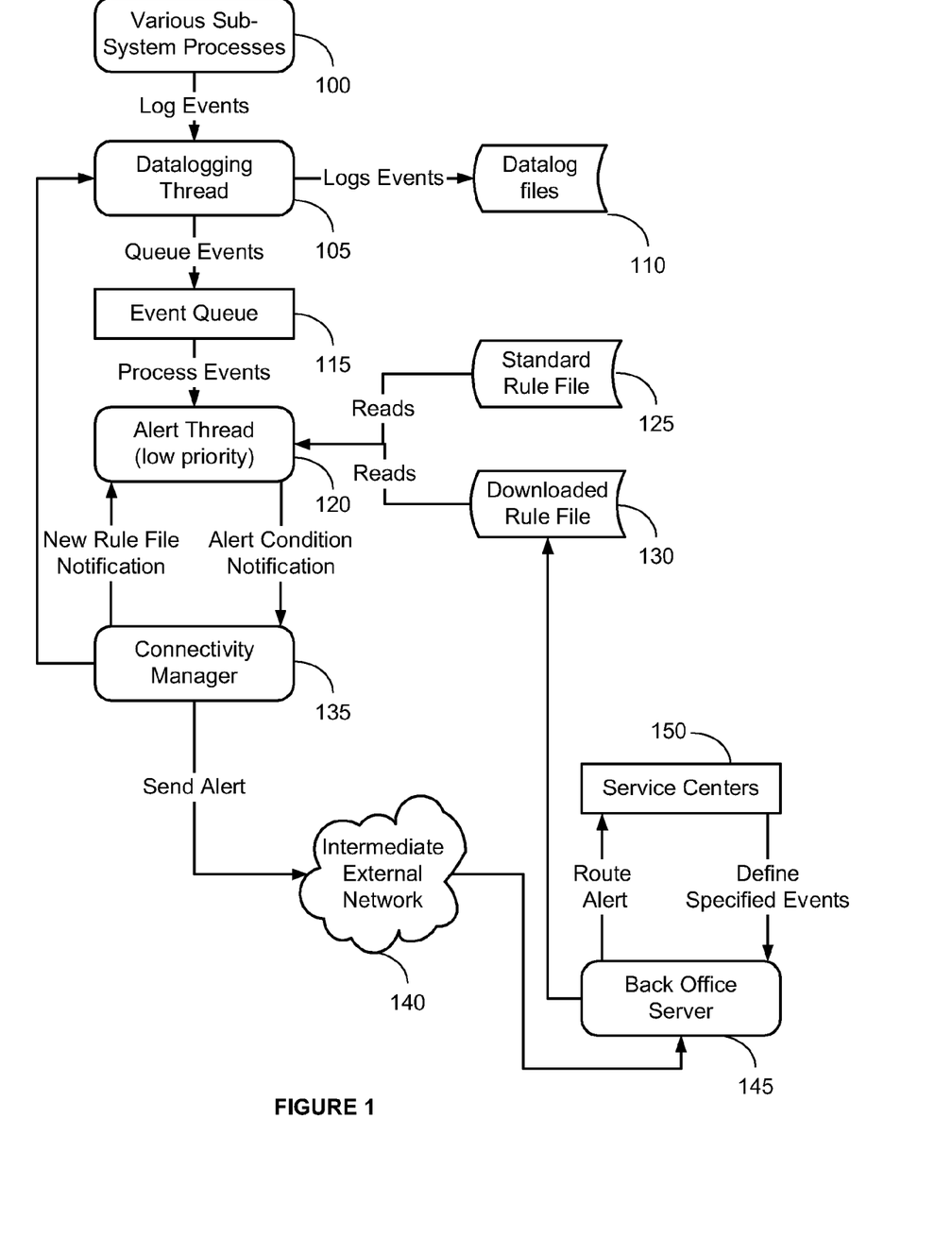
FIG. 1 illustrates a schematic of the processing modules and connectivity to the external monitor for a remote clinical diagnostic analyzer.
Figure 2:
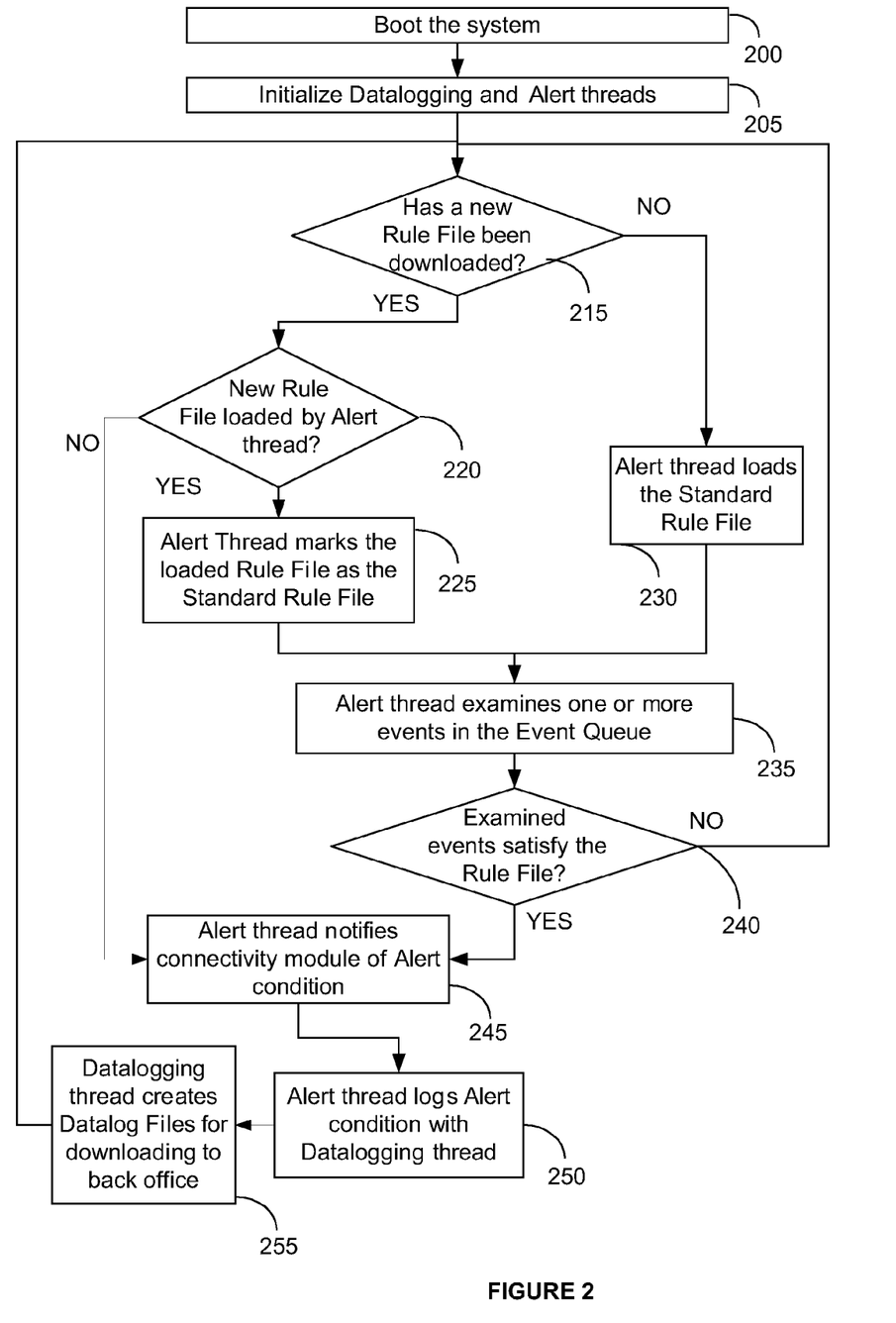
FIG. 2 illustrates some salient steps in generating customized real-time alerts in a preferred embodiment.

FIG. 1 illustrates a preferred embodiment. FIG. 2 illustrates an approximately corresponding basic flow of control in a method. This illustrative, preferred embodiment, provides for real-time alerts in response to dynamically customized events. The customized events may be defined to be a particular combination of basic events or signals generated at the clinical diagnostic analyzer. The customized events are encoded using XML such that some basic events or signals may be logically combined without requiring distinct tags for one or more logical operations. This is possible because in one aspect of the preferred embodiment the ordering of the XML instructions specifies the appropriate logical operation.

The preferred clinical diagnostic analyzer has Sub-processes 100 that generate a series of messages as they are executed. Many of these messages reflect basic events. Messages are logged by Datalogging Thread 105 in one or more Datalog Files 110, which are log files. Datalog Thread 105 is an example of a circuit for logging information to be sent to or retrieved by the external monitor.

The Datalog Thread 105 may either generate or facilitate queuing of events in Event Queue 115. Events so queued are processed by Alert Thread 120, which also reads Standard Rule File 125 and if available, a Downloaded Rule File 130 in order to process the queued events. Preferably, the Alert Thread 120 is assigned low priority to reduce its impact on system performance. The Alert Thread 120 includes instructions to setup and release resources such as memory buffers for implementing events included in a Rule File, which is necessary for actually detecting the customized and other events described by the Rule File.

Many aspects of the operation of Alert Thread 120 along with operation of Datalogging Thread 105 are illustrated in FIG. 2. Alert Thread 120 provides an example of a circuit for detecting customized events at the clinical diagnostic analyzer. Advantageously, steps 235 and 240 (described later) in FIG. 2 describe some of actions carried out by a circuit for detecting customized events at the clinical diagnostic analyzer.

As illustrated by FIG. 2, during step 200 the system boots up and, during step 205, initializes Alert Thread 120 and Datalogging Thread 105. Implementation of these processes as threads is preferable to reduce the penalty on system performance and to make the implementation robust.

During step 215 a determination is made as to whether a new Rule File has been downloaded. If a new Rule File has been downloaded, control flows to step 220. During step 220, if the new Rule File is loaded by Alert Thread 120, then, control flows to step 225. During step 225, the new Rule File is used in lieu of the Standard Rule File with control flowing to step 235. Alternatively, control flows to step 245 from step 220. During step 245 an Alert is flagged to communicate an error condition to the external monitor server. It should be noted that variations of this procedure may include marking the downloaded Rule File as the new 'Standard Rule File.'

On the other hand, if no new downloaded Rule File is detected during step 215, control flows to step 235 following the loading of the Standard Rule File.

During step 235 Alert Thread 120 examines one or more events in Event Queue 115 in view of the events, including any customized events in the loaded Rule File.

Returning to the description of the preferred embodiment, an exemplary Rule File is provided below to illustrate the XML tags and structure used to efficiently specify customized events:

```
<?xml version="1.0" ?>
- <ALERTCONFIG alertConfigId="SW43_V1.0"
alertConfigName="SW 4,3 V1.0">
  - <!--
    SS1 Thermal Current Out of Spec alerts when 1 is posted
    -->
  - <RULE ruleId="R1" ruleName="SS1 Thermal Current"
      rearmInterval="30" rearmIntervalUnits="MINUTES"
      econnectivityAction="ALERT">
  - <THRESHOLD eventType="214" thresholdCount="1"
      thresholdInterval="60" thresholdIntervalUnits="MINUTES">
    <CRITERIA parameterType="176" op="EQ" value="30"/>
    <CRITERIA parameterType="657" op="OUTSIDE"
      value="520"maxValue="770" />
    </THRESHOLD>
    </RULE>
  </ALERTCONFIG>
```

In the above event, the basic event evaluates the thermal current at a device. The various parameters are specified for triggering an event along with operations such as 'EQ' and 'OUTSIDE'. The number of times the parameters satisfy the prescribed ranges is specified by parameter 'thresholdCount'. The parameter thresholdInterval is important in conjunction with parameter thresholdCount. For instance, a count of 3 over 6 months may be treated differently that a count of 3 in one minute. The relevant time duration is specified by the parameter thresholdInterval. The following example illustrates a composite event requiring more than one times for a set of prescribed ranges to be satisfied:

```
<?xml version="1.0" ?>
- <ALERTCONFIG alertConfigId="SW43_V1.0"
alertConfigName="SW 4,3 V1.0">
  - <!--
    Slide Inc Cumulative Edge Problem alerts when more than 1 post in
    60 minutes
    -->
  - <RULE ruleId="R11" ruleName="Slide Inc Cumulative Edge"
      rearmInterval="30" rearmIntervalUnits="MINUTES"
      econnectivityAction="ALERT">
  - <THRESHOLD eventType="212" thresholdCount="2"
      thresholdInterval="60" thresholdIntervalUnits="MINUTES">
    <CRITERIA parameterType="651" op="LT" value="-60" />
    </THRESHOLD>
    </RULE>
  </ALERTCONFIG>
```

Advantageously, in a preferred embodiment, within the RULE tag all conditions specified by nested tags need to be satisfied concurrently to specify an event, the entire RULE tag by itself specifies an event. Thus, RULE tags at the same level of nesting are logically ORed while tags included within a RULE tag are logically ANDed. This allows complex events of interest to be built up by suitably combining basic events. Thus, not only can the RULE FILE be changed, but the events or conditions predefined for a clinical diagnostic analyzer serve as building blocks for formulating more complex events. Below is an example in which multiple customized events are defined in the same XML encoded Rule File:

```xml
<?xml version="1.0" ?>
<ALERTCONFIG alertConfigId="SW43_V1.0" alertConfigName="SW 4,3 V1.0">
 <!--
 SS1 Thermal Current Out of Spec alerts when 1 is posted
 -->
 <RULE ruleId="R1" ruleName="SS1 Thermal Current" rearmInterval="30"
      rearmIntervalUnits="MINUTES" econnectivityAction="ALERT">
 <THRESHOLD eventType="214" thresholdCount="1" thresholdInterval="60"
      thresholdIntervalUnits="MINUTES">
 <CRITERIA parameterType="176" op="EQ" value="30" />
 <CRITERIA parameterType="657" op="OUTSIDE" value="520" maxValue="770" />
   </THRESHOLD>
   </RULE>
 <!--
 SS2 Thermal Current Out of Spec alerts when 1 is posted
 -->
 <RULE ruleId="R2" ruleName="SS2 Thermal Current" rearmInterval="30"
      rearmIntervalUnits="MINUTES" econnectivityAction="ALERT">
 <THRESHOLD eventType="214" thresholdCount="1" thresholdInterval="60"
      thresholdIntervalUnits="MINUTES">
 <CRITERIA parameterType="176" op="EQ" value="22" />
 <CRITERIA parameterType="657" op="OUTSIDE" value="520" maxValue="770" />
   </THRESHOLD>
   </RULE>
 <!--
 Slide Inc Thermal Current out of Spec alerts when 1 is posted
 -->
 <RULE ruleId="R3" ruleName="Slide Inc Thermal Current" rearmInterval="30"
      rearmIntervalUnits="MINUTES" econnectivityAction="ALERT">
 <THRESHOLD eventType="214" thresholdCount="1" thresholdInterval="60"
      thresholdIntervalUnits="MINUTES">
 <CRITERIA parameterType="176" op="EQ" value="5" />
 <CRITERIA parameterType="657" op="OUTSIDE" value="500" maxValue="630" />
   </THRESHOLD>
   </RULE>
 <!--
 Primary Tip Sealer Current out of Spec alerts when 1 is posted
 -->
 <RULE ruleId="R4" ruleName="Primary Tip Sealer Current" rearmInterval="30"
      rearmIntervalUnits="MINUTES" econnectivityAction="ALERT">
 <THRESHOLD eventType="214" thresholdCount="1" thresholdInterval="60"
      thresholdIntervalUnits="MINUTES">
 <CRITERIA parameterType="176" op="EQ" value="42" />
 <CRITERIA parameterType="657" op="OUTSIDE" value="63" maxValue="83" />
   </THRESHOLD>
   </RULE>
</ALERTCONFIG>
```

The parameter 'ruleName' conveniently represents composite event defined for the clinical diagnostic analyzer using 'THRESHOLD eventType'. VITROS 5600™ and VITROS 3600™ clinical diagnostic analyzer support a large number of THRESHOLD eventType descriptors for monitoring and operating the multiple devices and subsystems in the clinical diagnostic analyzer.

In the preferred embodiment, tag "RULE" describes a composite event. A configuration file or Rule File, substantively indicated by the "ALERTCONFIG" tag, is limited to sixty-four (64) such composite events. For each such event, a maximum of ten (10) thresholds may be specified using the "THRESHOLD" tag. Further, for each THRESHOLD tag, no more than 5 criteria can be specified using the "CRITERIA" tag. In summary, a tag describes the customized event. Nested within this tag are a set of threshold specifications, such as exceeding a value 'n' number of times within 'm' units of time and the like. For each of the threshold specifications, operations are performed using detected parameters in accordance with specified criteria, preferably presented in tags further nested therein. As is readily appreciated, these are implementations specific details and can be readily modified in different implementations.

An example basic event is described in the table below:

| THRESHOLD eventType | Name of event | Applicable Parameters | Corresponds to |
|---|---|---|---|
| 214 | THERMO_DEVICE_CURRENT | 1 | Time Stamp |
| | | 176 | Device being controlled |
| | | 657 | Value of the Current |

In the table above, a basic event 'THERMO_DEVICE_CURRENT,' which is used to monitor the current of thermal control devices, is described. This basic event has a numeric code '214 assigned to it. Further, as indicated, it accepts three parameters: a time stamp, identity of the device for which the current is being monitored, and the value of the current. As seen in the XML description above, for device 42 the thermal current is monitored and if it is outside the range 63 to 83, an event is recognized. Because the thresholdCount is set to 1, any single such occurrence is sufficient to trigger an Alert.

The following exemplary RULE FILE combines two predefined basic events corresponding to two distinct THRESHOLD eventType codes/parameters using a logical AND operation. The AND operation is implied by the placement of both THRESHOLD eventType codes within a single RULE tag at the same nesting level.

```
<?xml version="1.0" ?>
- <ALERTCONFIG alertConfigId="SW43_V1.0"
alertConfigName="SW 4,3 V1.0">
  - <!--
    CC PW8-030 is posted in the same hour as that the min cumulative
      edge error occurs
    -->
- <RULE ruleId="R15" ruleName="Black Dust" rearmInterval="30"
    rearmIntervalUnits="MINUTES" econnectivityAction="ALERT">
- <THRESHOLD eventType="212" thresholdCount="1"
    thresholdInterval="60" thresholdIntervalUnits="MINUTES">
  <CRITERIA parameterType="651" op="LT" value="-60" />
  </THRESHOLD>
- <THRESHOLD eventType="111" thresholdCount="1"
    thresholdInterval="60" thresholdIntervalUnits="MINUTES">
  <CRITERIA parameterType="134" op="EQ" value="PW8" />
  <CRITERIA parameterType="135" op="EQ" value="030" />
  </THRESHOLD>
  </RULE>
  </ALERTCONFIG>
```

Returning to FIG. 2, during step 235 Alert Thread 120 applies the events specified in the Rule File to identify if an alert of interest needs to be generated. To allow the various definitions of events to be computed over many operations in the clinical diagnostic analyzer, preferably multiple dedicated memory locations are allocated to provide the buffers to track and count events.

During step 240 Alert Thread 120 determines if the examined events satisfy the Rule File. If no events satisfied the Rule File, i.e., lead to the generation of an alert, control flows back to step 215. Alternatively, if upon examination of an event the Rule File is satisfied, Alert Thread 120 notifies a Connectivity Manager 135 of an Alert condition during step 245. Connectivity Manager 135 provides an example of a circuit for communicating with the external monitor.

Further, Alert Thread 120 logs the Alert condition with Datalogging Thread 105 during step 250 followed by creation or updating of Datalog Files during step 255. Control passes back to step 215 from step 255 for continued monitoring of the analyzer.

An alert, e.g., by HTTP Post command, generated and sent by Connectivity Manager 135, informs the external monitoring system that log files have useful and pertinent information relating to a customized event. The external monitoring system can, then, download them for further action, such as scheduling a service call. Alternatively, the identified data may be subject to further analysis. Often, an authorized individual at the back office housing the external monitor may initiate the downloading of log files.

Connectivity Manager 135, which preferably is a connection sub-module providing a link to the external monitoring system, in FIG. 1 sends messages by utilizing a virtual private networking link to securely traverse an external intermediate network, such as the Internet, to deliver the messages to the Back Office Server 145. Back Office Server 145, in turn, forwards alerts or other related tasks to Service Centers 150 where the data is analyzed and acted upon. Back Office Server 145 determines, preferably based on the device, where to route the message and then may sends an email to the appropriate service center or individual.

Figure 3:
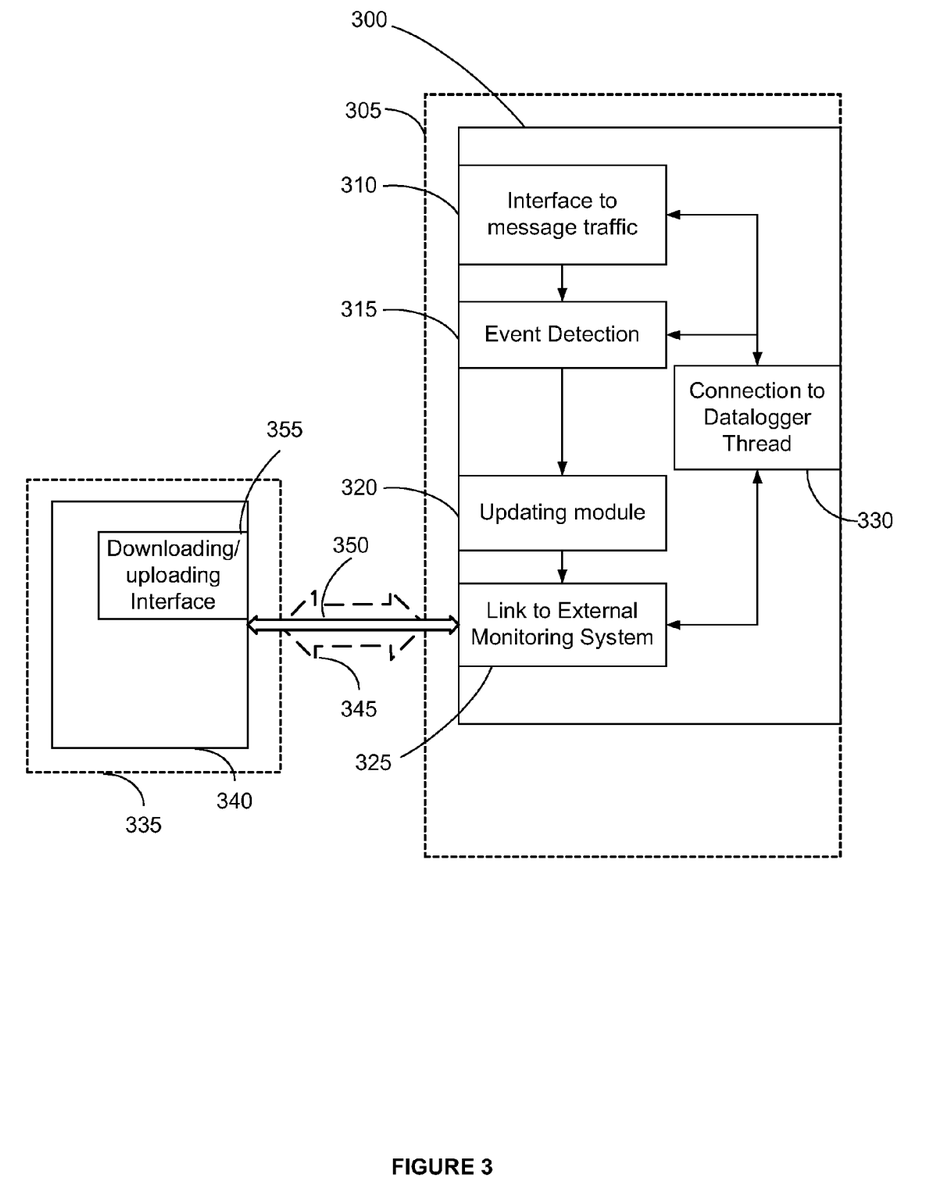
FIG. 3 illustrates a schematic of the processing modules and connectivity to the external monitor for a remote clinical diagnostic analyzer.

FIG. 3 illustrates some aspects of a preferred embedded module. Module 300 in Network 305 comprises an Interface to Message Traffic 310, a sub-module for Event Detection 315, a sub-module Updating 320 for processing updates, for instance to customize events. Module 300 also comprises a sub-module for Link to External Monitoring System 325 and a Connection to Datalogger Thread 330. Network 305 is connected to Network 335 containing the External Monitoring System 340 via a connection 345. External Monitoring System 340 is connected to Sub-module for Link to External Monitoring System 325 via Tunneling link 350. External Monitoring System 340 includes a sub-module Downloading/Uploading Interface 355 for managing the uploading and downloading of data and instructions to customize events by Module 300.

Figure 5:
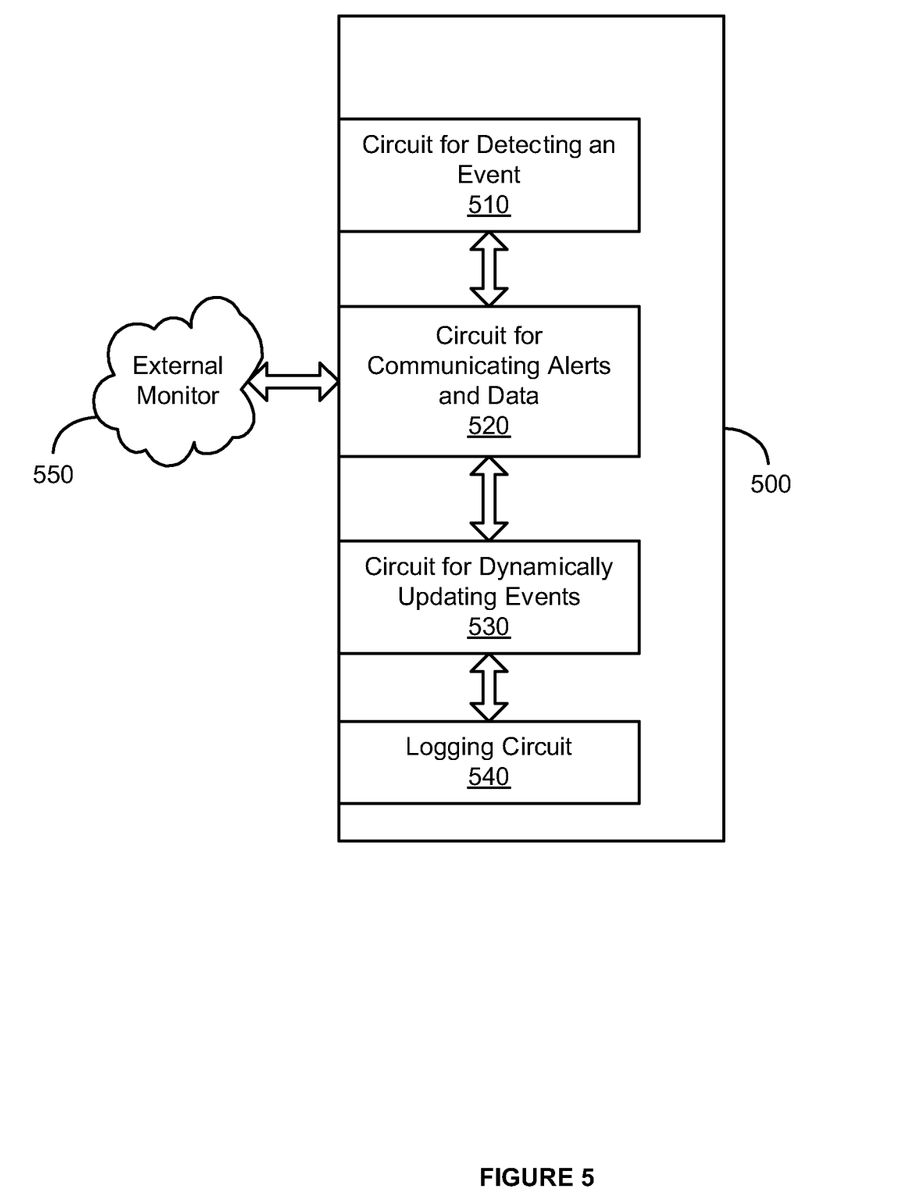
FIG. 5 illustrates a schematic of the processing modules and connectivity to the external monitor for a remote clinical diagnostic analyzer.

A Module 500 for communicating real-time alerts generated at a clinical diagnostic analyzer is illustrated in FIG. 5 as comprising a Circuit for detecting an Event 510, which is in communication with Circuit for Communicating Alerts and Data 520. Circuit for Communicating Alerts and Data 520 manages communications with External monitor 550. Circuit for Communicating Alerts and Data 520 communicates with Circuit for Dynamically Updating Events 530 to provide newly received Rule files with updated event definitions.

Figure 4:
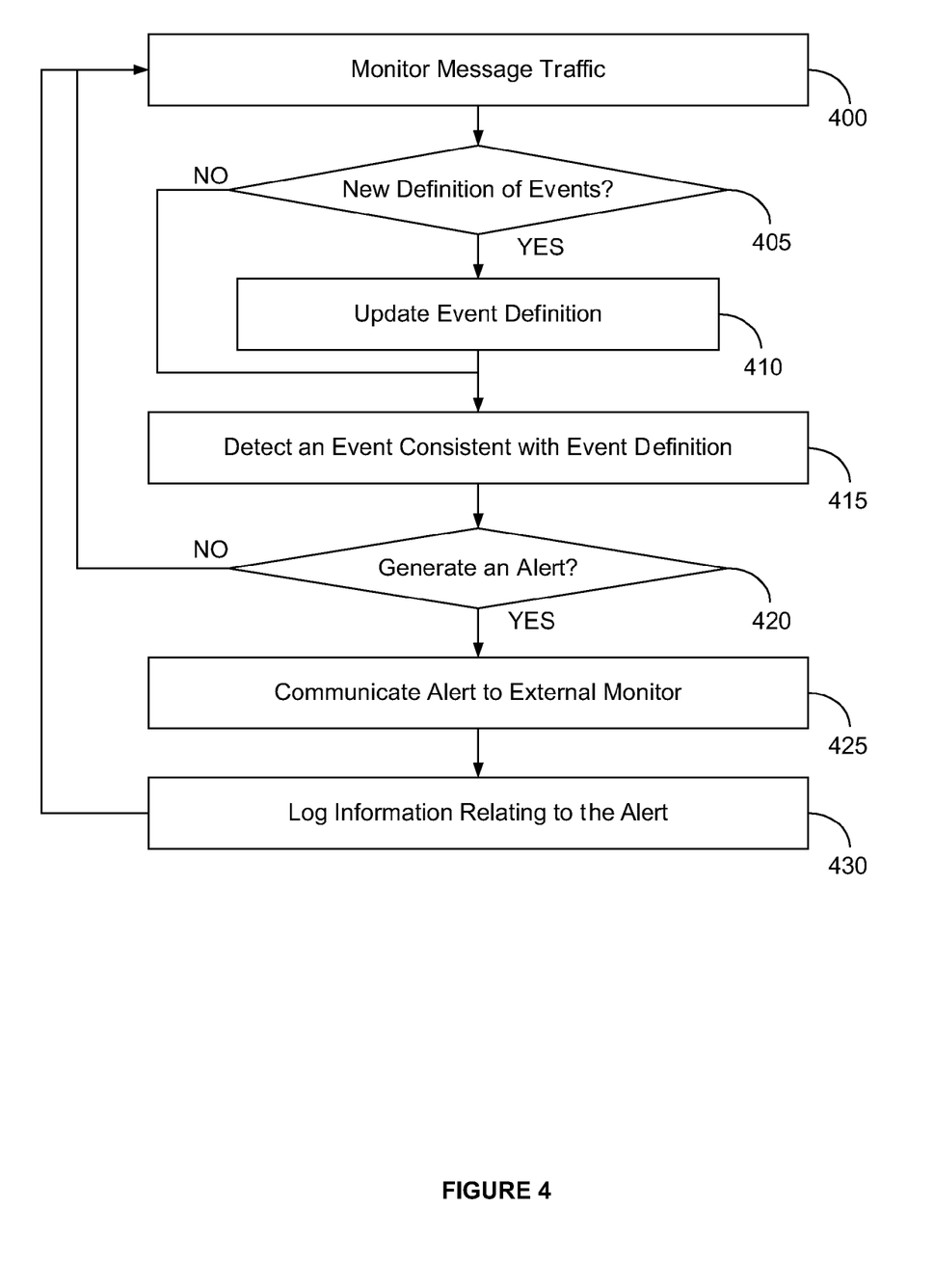
FIG. 4 illustrates some salient steps in generating customized real-time alerts in a preferred embodiment.

Although, it is preferred that an entire Rule File be received with definitions of all alertable events, it is within the scope of the claims to have updates to supplement a Rule File. This aspect is illustrated in FIG. 4 which shows event monitoring in step 400 with control passing to step 405 decision step to determine if a new event definition is present. In the event a new definition is present, Event definition is updated during step 410, which may be by replacing a Rule File or merely supplementing or modifying definitions by other means. Control from steps 405 or 410 passes to step 415 as shown for the detection of an event. During step 420 the event is evaluated to determine if the event is alertable. If not alert is to be issued, control passes back to step 400. Else, control passes to step 425, during which an alert is communicated to an External Monitor with information relating to the alertable event logged during step 430.

Returning to FIG. 1, Service Centers 150 may provide alternative definitions of events to be incorporated into Rule File 125, which is sent to the embedded module for future event flagging. Steps 215 through 230 in FIG. 2 provide further details of an exemplary circuit for implementing changes in the customized events. In general, Rule Files can be built externally and sent down to one or more embedded modules. This can be done in order to identify scenarios other than those covered by the Standard Rule File.

The Back Office Server 145 tells the clinical diagnostic analyzer that a new Rule File has been downloaded. This causes Alert Thread 120 to load the downloaded rule file and use it instead of the Standard Rule File in software. Failures to load this file is an alertable event as is shown in FIG. 2 (flow of control from step 220 to step 245).

Thus, the Rule file structure allows for the creation of rules that are more flexible than the familiar inflexible single (or a precious few) threshold rule (e.g., if the incubator temp>35 then send alert). In general, in a preferred embodiment, it is possible to flag events such as:

(i) A specific event occurring (e.g., a power down, a Software load).

(ii) A specific event occurring with conditions on specific attributes of the event (e.g., System Environmental event is logged and the ambient temp sensor has a value>40, the power up event occurs and the proper shutdown flag is not set to true).

(iii) A group of events occurs as specified above within a specified time frame (e.g., 60 seconds). And, (iv) A prescribed number of occurrences of an event, such as a threshold being exceeded five times in an hour.

Further, although not illustrated in FIG. 2, if the in-memory events queue buffering events for processing reaches its maximum size, it sends an Alert message to the Back Office Server 145 via Connectivity Manager 135 to inform the Back Office Server 145 of its temporary inability to process events.

Alert Thread 120 preferably has built in protection from retriggering the same event multiple times within a specific timeframe (e.g. 30 minutes unless the rule sets it differently). This prevents a cascading effect that could push thousands of alerts downstream.

As noted, rules can be configured to tell the external monitor to retrieve the most recent log files. This request is sent in addition to the message and is useful if the condition is going to warrant further data analysis.

In a preferred embodiment, security and privacy in enhanced, for instance in the event a security breach is detected or even suspected, by allowing an operator to turn off the real-time Alert messages to controllably isolate the embedded module.

One skilled in the art will appreciate that the above disclosure is susceptible to many variations and alternative implementations without departing from its teachings or spirit. The scope of the claims appended below includes such modifications. Further, each reference discussed and cited herein is hereby incorporated herein by reference in its entirety.

We claim:

1. A module for communicating real-time customizable alerts at a clinical diagnostic analyzer to an external monitor, the module comprising:
    a customized event detection sub-module embodied in hardware computer in the clinical diagnostic analyzer, wherein customized events include a first event, wherein a customized event comprises a specified logical combination of basic events, each basic event reflects a detection of a descriptor of the state of the colonial diagnostic analyzer, whereby customized facilitate maintenance of the clinical diagnostic analyzer;
    a connection sub-module embodied in hardware computer providing a link to the external monitor, wherein the external monitor, linked to the clinical diagnostic analyzer via a secure connection, receives an alert in response to the detection of the first event, wherein the alert does not include patient identifying information;
    a sub-module embodied in hardware computer for dynamically updating customized events to be detected to include a second event; and
    a data-logging facility embodied in hardware computer for logging information to be sent to or retrieved by the external monitor; wherein instructions to define the second event are communicated via instructions coded in a markup language to perform at least one of (a) dynamically modify a customized event, (b) add a new event, and (c) add a customized event.

2. The module of claim 1, the markup language is eXtensible Markup Language.

3. The module of claim 2, wherein at least one logical operation is encoded in the order of tags in the eXtensible Markup Language.

4. The module of claim 2, wherein the second event is a customized event defined by a logical combination of two or more basic events.

5. The module of claim 1, wherein the module has at least two network addresses, one address in a first network different from a second address in a second network; wherein clinical diagnostic analyzer is networked into the second network and the external monitor is in the second network.

6. The module of claim 5, wherein the module is connected to the external monitor via a virtual private networking link.

7. The module of claim 6, wherein sub-module with access to message traffic does not have access to patient identifying data on the clinical diagnostic analyzer.

8. The module of claim 6, wherein the module is addressable as part of a subnet of the first network by the external monitor, wherein the subnet is protected by a firewall from another subnet in the first network.

9. A module for communicating real-time alerts generated at a clinical diagnostic analyzer to an external monitor, the module comprising:
    a circuit for detecting a customized event at the clinical diagnostic analyzer; wherein the customized event comprises a specified logical combination of basic events, each basic event reflects a detection of a descriptor of the state of the clinical diagnostic analyzer, whereby customized events facilitate maintenance of the clinical diagnostic analyzer;
    a circuit for communicating an alert to the external monitor; wherein customized events include a first event, wherein the external monitor, linked to the clinical diagnostic analyzer via a secure connection, receives the alert in response to the detection of the first event, wherein the alert does not include patient identifying information;
    a circuit for dynamically updating customized events event; a circuit for logging information to be sent or retrieved by the external monitor; and
    wherein the circuit for dynamically updating customized events receives specifications of a second event from the circuit for communicating the alert to the external monitor as instructions coded in eXtensible Markup Language, wherein the circuit for communicating the alert also receives instructions updating customized events.

10. The module of claim 9, wherein at least one logical operation specified in the instructions is encoded in the order of tags in the eXtensible Markup Language.

11. The module of claim 10, wherein the circuit for communicating the alert to the external monitor uses a tunnel defining a link between the module and the external monitor.

12. The module of claim 10, wherein the circuit for logging information external monitor updates a log file in response to detection of a customized event.

13. The module of claim 9, wherein the module has at least one address in a first network, and a second address in a second network, the first network being different from the second network.

14. The module of claim 13, wherein the circuit for dynamically updating customized events causes the circuit for detecting customized events to detect an updated customized event.

15. A method performed at a module for communicating real-time alerts generated at a clinical diagnostic analyzer to an external monitor, the method comprising facilitating the steps of:
    detecting a customized event at the clinical diagnostic analyzer; wherein a customized event comprises a specified logical combination of the basic events, each basic event reflects a detection of a descriptor of the state of the clinical diagnostic analyzer, whereby customized events facilitate maintenance of the clinical diagnostic analyzer;

communicating in real-time, in response to detection of the customized event, an alert to the external monitor, wherein the external monitor is linked to the clinical diagnostic analyzer via a secure network connection, and wherein furthermore the alert does not include patient identifying information;

updating customized events to include a second event in response to an instruction received from the external monitor; and logging information to be sent to or retrieved by the external monitor, wherein instructions to define the second event are communicated via instructions coded in a markup language to perform at least one of (a) dynamically modify a customized event, (b) add a new event, and (c) add the customized event.

16. The method of claim 15, wherein the clinical diagnostic analyzer has at least one address in a first network and another address in a second network.

17. The method of claim 15, wherein logging information includes writing to a log file conditions relating to the detected customized event.

18. The method of claim 15, wherein the instructions describing the second event are coded in eXtensible Markup Language such that at least one logical operation specified by the instructions is encoded in the order of tags in the eXtensible Markup Language.

19. The method of claim 18 further comprising the step of describing the customized event using nested tags identifying the customized event, the thresholds used to define the composite event and a set of criteria describing logical operations performed using detected parameters.

* * * * *